(12) United States Patent
Li et al.

(10) Patent No.: US 8,183,378 B2
(45) Date of Patent: May 22, 2012

(54) LIGANDS, THEIR PREPARATION AND USES THEREOF IN ASYMMETRIC REACTIONS

(75) Inventors: Chao-Jun Li, Brossard (CA); Jianqing Feng, Suzhou (CN)

(73) Assignee: Chao-Jun Li, Brossard (CA)

( * ) Notice: Subject to any disclaimer, the term of this patent is extended or adjusted under 35 U.S.C. 154(b) by 671 days.

(21) Appl. No.: 12/267,285

(22) Filed: Nov. 7, 2008

(65) Prior Publication Data

US 2009/0247757 A1 Oct. 1, 2009

Related U.S. Application Data

(60) Provisional application No. 60/986,195, filed on Nov. 7, 2007.

(51) Int. Cl.
*C07D 217/02* (2006.01)

(52) U.S. Cl. .................................................. 546/149

(58) Field of Classification Search .................. None
See application file for complete search history.

(56) References Cited

FOREIGN PATENT DOCUMENTS

WO WO 2007019942 A1 * 2/2007

OTHER PUBLICATIONS

Machine Translation of WO 2007019942 A1, Feb. 2007.*
Alvarez et al., "Product Class 5: Isoquinolines," In: *Science of Synthesis*, D. StC. Black, Ed., 15: 661-838, 2005.
Brunel, "BINOL: A versatile chiral reagent," *Chem. Rev.*, 105:857-897, 2005.
Brunel, "BINOL: A versatile chiral reagent," Additions and Corrections, *Chem. Rev.*, 105: 4233, 2005.
Chrzanowska et al., "Asymmetric synthesis of isoquinoline alkaloids," *Chem. Rev.*, 104 (7): 3341-3370, 2004.
Feng et al., "Synthesis of a new chiral amino phosphine ligand and its application int he asymmetric allylic alkylation (AAA) reaction," *Tetrahedron: Asymmetry*, 18: 1043-1047, 2007.
Fernandez et al., "Catalytic asymmetric hydroboration/amination and alkylamination with rhodium complexes of 1,1'-(2-diarylphosphino-1-naphthyl)isoquinolin," *Chem. Eur. J.*, 6 (10): 1840-1846, 2000.
Gommermann et al., "Enantioselective, copper(I)-catalyzed three-component reaction for the preparation of propargylamines," *Angew. Chem. Int. Ed Engl.*, 42: 5763-66, 2003.
Larsen et al., "A modified Bischler-Napieralski procedure for the synthesis of 3-aryl-3,4-dihydroisoquinolines," *J. Org. Chem.*, 56:6034-6038, 1991.

Macleod et al., "Solvent-free direct aza-Friedel-Crafts ractions between 3,4-dihydroisoquinoline and 1- or 2-naphthols," *Tetrahedron Lett.*, 47: 67916794, 2006.
Noyori, "Catalytic Hydrogenation: A core technology in synthesis," *Adv. Synth. Catal.*, 345(1+2):1, 2003.
Pelletier and Cava, "Synthesis of the marine alkaloids aaptamine and demethyloxaaptamine and of the parent structure didemethoxyapptamine," *J. Org. Chem.*, 52:616-622, 1987.
Stille et al., "4-Methoxy-4'-Nitrobiphenyl [,1,'-Biphenyl,4-methoxy-4'-nitro-]" *Organic Synthese, Coll.*, vol. 9:533 (1998); vol. 71:97 (1993).
Takaya et al., "(R)-(+) and (S)-(-)2,2'-Bis_diphenylphosphino)-1,1'-binaphthyl (BINAP)," *Org. Synth., Coll.* vol. 8:57 (1993); vol. 67:20 (1989).
Valk et al., "Catalytic asymmetric hydroboration with heterotopic P-N ligands: Trends in enantioselectivity with increased steric demand," *Tetrahedron: Asymmetry*, 6: 2593-2596, 1995.
Zhu et al., "4-Nitrophenyltriflate as a new triflating agent," *Tetrahedron Letters*, 38(7):1181-1182, 1997.

* cited by examiner

*Primary Examiner* — Zinna Northington Davis
(74) *Attorney, Agent, or Firm* — Fulbright & Jaworski L.L.P.

(57) ABSTRACT

Novel chemical agents are described herein. More a ligand of general Formula I:

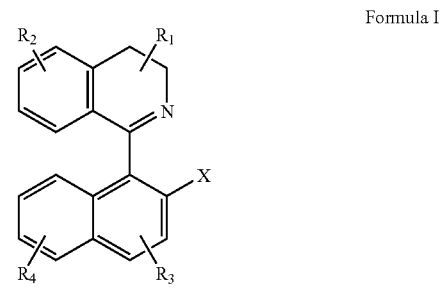

Formula I wherein $R_1$, $R_2$, $R_3$ and $R_4$, are independently selected from the group consisting of hydrogen, halogen, hydroxy, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkylthio, $C(O)R_5$, $C(O)OR_5$, $C(O)NHR_5$, $Si(R_5)_3$, benzyl and aryl; X is selected from the group consisting of Cl, Br, I, $OR_6$, O-Prot, $OPR_6$, $P(R_6)_2$, $NHR_6$, $N(R_6)_2$, $NHCSNHR_6$, $NHCONHR_6$ and $SR_6$; and $R_5$ and $R_6$ are independently selected from the group consisting of hydrogen, $C_{1-10}$ alkyl, $C_{2-10}$ alkenyl, $C_{2-10}$ alkynyl, $C_{1-10}$ alkoxy, phenyl, and aryl. These ligands are useful in asymmetric reactions as well as in asymmetric synthesis of molecules of biological interest.

21 Claims, No Drawings

LIGANDS, THEIR PREPARATION AND USES THEREOF IN ASYMMETRIC REACTIONS

CROSS REFERENCE TO RELATED APPLICATIONS

The present application claims the benefit of U.S. Provisional Application No. 60/986,195 filed Nov. 7, 2007, the entire contents of which are incorporated by reference.

FIELD

The present invention broadly relates to ligands. More specifically, but not exclusively, the present invention relates to ligands, their preparation and use in asymmetric reactions. Yet more specifically, but not exclusively, the present invention relates to N, N; N, O; N, S; N, halogen; and N, P ligands, their preparation and use in asymmetric reactions.

BACKGROUND

Asymmetric reactions represent one of the most important developments of modern organic chemistry.[1] Asymmetric reactions enable the synthesis of optically active compounds, which are highly desirable in the field of organic chemistry, and particularly in the pharmaceutical industry. Indeed, many drugs are required to be produced as single enantiomers (e.g. high optical purity), since it is often observed that only one of the enantiomers possesses the desirable drug profile. With the growing demand for effective and potent drugs, the development of novel asymmetric reactions has become paramount for the production of enantiomerically pure compounds.

Catalytic asymmetric reactions take advantage of chiral catalysts to produce enantiomerically pure or enriched compounds. The catalyst's chirality can originate from coordination to a chiral ligand. Examples of chiral ligands include BINAP,[2] QUINAP,[3] and BINOL[4] (Scheme 1). These ligands can provide excellent enantioselectivity for various reactions, and have proven to be particularly effective in catalyzing asymmetric reactions when coordinated to transition metals.

A new class of chiral ligands for catalytic asymmetric reactions and other applications, including 1-(1,2,3,4-tetrahydroisoquinolin-1-yl)-naphthalen-2-ol (THIQNOL, Scheme 1), was disclosed by Li et al. in PCT/CA2007/000348, published under WO 2007/098608 A1.[5,6]

Scheme 1

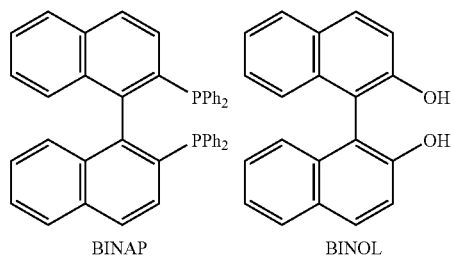

BINAP          BINOL

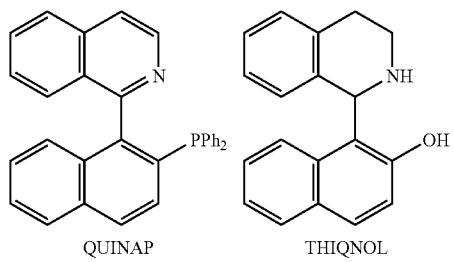

QUINAP          THIQNOL

The present invention refers to a number of documents, the content of which is herein incorporated by reference in their entirety.

SUMMARY

The present invention broadly relates to a novel class of ligands. More specifically, but not exclusively, the present invention relates to chiral N, N; N, O; N, S, N, halogen; and N, P ligands. Yet more specifically, but not exclusively, the present invention relates to chiral ligands based on the 1-(3,4-dihydroisoquinolin-1-yl)-naphthalene core structure.

In an embodiment, the present invention relates to a ligand of general Formula I:

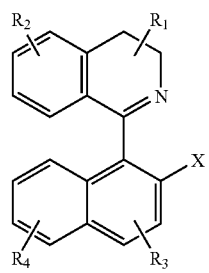

Formula I wherein:

$R_1$, $R_2$, $R_3$ and $R_4$, are independently selected from the group consisting of hydrogen, halogen, hydroxy, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkylthio, $C(O)R_5$, $C(O)OR_5$, $C(O)NHR_5$, $Si(R_5)_3$, benzyl and aryl;

X is selected from the group consisting of Cl, Br, I, $OR_6$, O-Prot, $OPR_6$, $P(R_6)_2$, $NHR_6$, $N(R_6)_2$, $NHCSNHR_6$, $NHCONHR_6$ and $SR_6$; and $R_5$ and $R_6$ are independently selected from the group consisting of hydrogen, $C_{1-10}$ alkyl, $C_{2-10}$ alkenyl, $C_{2-10}$ alkynyl, $C_{1-10}$ alkoxy, phenyl, and aryl.

In an embodiment, the present invention relates to ligands selected from the group consisting of:

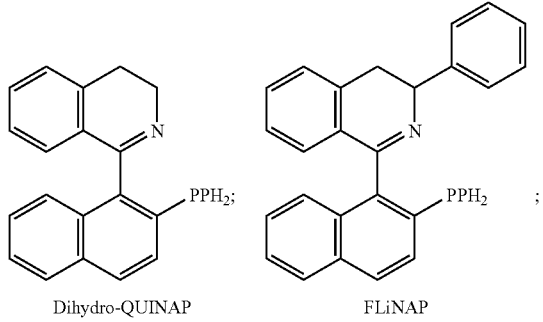

Dihydro-QUINAP          FLiNAP

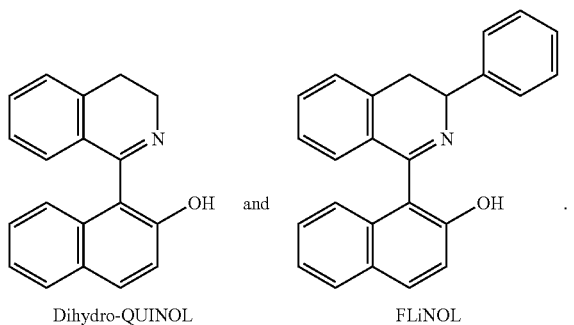

Dihydro-QUINOL          FLiNOL

In an embodiment, the present invention relates to a racemic mixture of a ligand of general Formula I.

In an embodiment, the present invention relates to a non-racemic mixture of a ligand of general Formula I.

In an embodiment, the present invention relates to a ligand of general Formula I comprising both (+) and (−)-stereoisomers.

In an embodiment, the present invention relates to a ligand of general Formula I comprising the (+)-stereoisomer.

In an embodiment, the present invention relates to a ligand of general Formula I comprising the (−)-stereoisomer.

In an embodiment, the present invention relates to a ligand of general Formula I comprising both (+) and (−)-enantiomers.

In an embodiment, the present invention relates to a ligand of general Formula I comprising the (+)-enantiomer.

In an embodiment, the present invention relates to a ligand of general Formula I comprising the (−)-enantiomer.

In an embodiment, the present invention relates to a ligand of general Formula I comprising both R- and S-enantiomers.

In an embodiment, the present invention relates to a ligand of general Formula I comprising the R-enantiomer.

In an embodiment, the present invention relates to a ligand of general Formula I comprising the S-enantiomer.

In an embodiment, the present invention relates to a process for the preparation of a ligand of general Formula I:

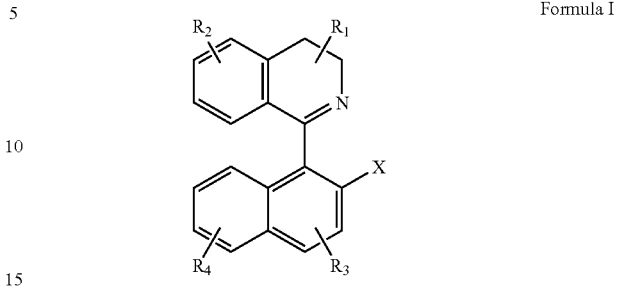

Formula I wherein:
$R_1$, $R_2$, $R_3$ and $R_4$, are independently selected from the group consisting of hydrogen, halogen, hydroxy, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkylthio, $C(O)R_5$, $C(O)OR_5$, $C(O)NHR_5$, $Si(R_5)_3$, benzyl and aryl;

X is selected from the group consisting of Cl, Br, I, $OR_6$, O-Prot, $OPR_6$, $P(R_6)_2$, $NHR_6$, $N(R_6)_2$, $NHCSNHR_6$, $NHCONHR_6$ and $SR_6$; and $R_5$ and $R_6$ are independently selected from the group consisting of hydrogen, $C_{1-10}$ alkyl, $C_{2-10}$ alkenyl, $C_{2-10}$ alkynyl, $C_{1-10}$ alkoxy, phenyl, and aryl;

comprising: i) reacting a compound of general Formula Ia:

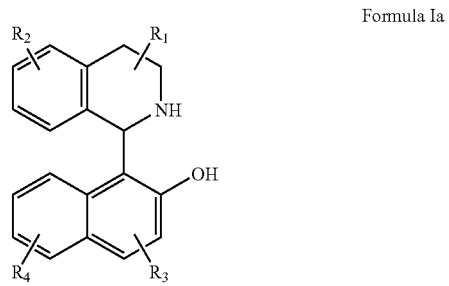

Formula Ia wherein:
$R_1$, $R_2$, $R_3$ and $R_4$, are independently selected from the group consisting of hydrogen, halogen, hydroxy, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkylthio, $C(O)R_5$, $C(O)OR_5$, $C(O)NHR_5$, $Si(R_5)_3$, benzyl and aryl; and $R_5$ is selected from the group consisting of hydrogen, $C_{1-10}$ alkyl, $C_{2-10}$ alkenyl, $C_{2-10}$ alkynyl, $C_{1-10}$ alkoxy, phenyl, and aryl;

with a triflating reagent to produce a compound of general Formula Ib:

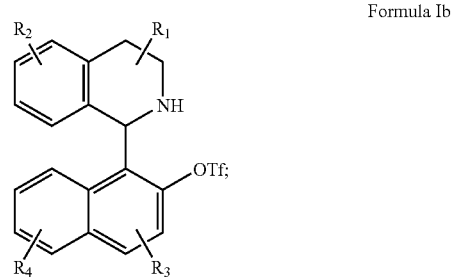

Formula Ib ii) reacting the compound of general Formula Ib with an oxidant to produce a compound of general Formula Ic:

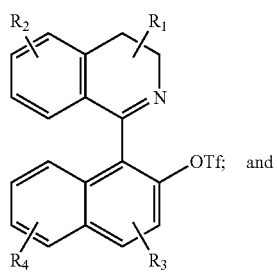

Formula Ic iii) converting the triflate to produce a ligand of general Formula I.

In an embodiment, the present invention relates to the use of a ligand of general Formula I in asymmetric reactions.

In an embodiment, the present invention relates to the use of a ligand of general Formula I in catalytic asymmetric reactions.

In an embodiment, the present invention relates to the use of a ligand of general Formula I in asymmetric synthesis.

In an embodiment, the present invention relates to the use of a ligand of general Formula I in catalytic asymmetric synthesis.

In an embodiment, the present invention relates to the use of a ligand of general Formula I in the asymmetric synthesis of biologically active compounds.

In an embodiment, the present invention relates to the use of a ligand of general Formula I in the asymmetric catalytic synthesis of biologically active compounds.

The foregoing and other objects, advantages and features of the present invention will become more apparent upon reading of the following non restrictive description of illustrative embodiments thereof, given by way of example only.

DETAILED DESCRIPTION

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "carbonyl" as used herein, represents a C(O) group, which can also be represented as C=O.

The terms "carboxy" or "carboxyl," as used interchangeably herein, represents a $CO_2H$ group.

The term "halogen" as used herein is understood as referring to fluorine, chlorine, bromine, or iodine. Correspondingly, the meaning of the term "halo" is understood to encompass fluoro, chloro, bromo, and iodo.

The term "hydroxy" or "hydroxyl," as used interchangeably herein, represents an —OH group.

The term "alkyl group" as used herein is understood as referring to a saturated, monovalent unbranched or branched hydrocarbon chain or ring. Examples of alkyl groups include, but are not limited to, $C_{1-10}$ alkyl groups. Examples of $C_{1-10}$ alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, cyclohexyl, heptyl, octyl, nonyl and decyl.

The term "alkenyl" as used herein is understood as referring to monovalent straight or branched chain groups of, unless otherwise specified, from 2 to 10 carbons, such as, for example, 2 to 6 carbon atoms or 2 to 4 carbon atoms, comprising one or more carbon-carbon double bonds and is exemplified by ethenyl, 1-propenyl, 2-propenyl, 2-methyl-1-propenyl, 1-butenyl, 2-butenyl and the like.

The term "alkynyl" as used herein is understood as referring to monovalent straight or branched chain groups of from 2 to 10 carbon atoms comprising one or more carbon-carbon triple bonds and is exemplified by ethynyl, 1-propynyl, and the like.

The terms "alkoxy" or "alkyloxy," as used interchangeably herein, represent an alkyl group attached to the parent molecular group through an oxygen atom. Exemplary alkoxy groups comprise from 1 to 10 carbons.

The term "alkylthio," as used herein, represents an alkyl group attached to the parent molecular group through a sulfur atom. Exemplary alkylthio groups comprise from 1 to 10 carbon atoms.

The term "aryl" as used herein is understood as referring to 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions. Aryl groups can also be part of a polycyclic group. For example, aryl groups include fused aromatic moieties such as naphthyl, anthracenyl, quinolyl, indolyl, and the like.

The term "protecting group" or "prot" as used in the present specification has the meaning usual in synthetic chemistry, particularly for hydroxyl group protection. It refers to any group that may be covalently bound to a hydroxy group, protecting it from undesirable reactions during synthetic procedures. Commonly used hydroxyl-protecting groups are disclosed in Greene, "Protective Groups In Organic Synthesis, 3$^{rd}$ Edition" (John Wiley & Sons, New York, 1999), which is incorporated herein by reference. Non-limiting suitable protecting groups include t-butyl ethers, benzyl ethers, silyl ethers, MOM (methoxy methyl ethers), MEM (2-methoxy ethoxy methyl ethers) and acetates.

As used in this specification, the term "isomer" refers to compounds that have the same molecular formula but differ in the nature or sequence of bonding of their atoms or the arrangement of their atoms in space. Isomers in which the connectivity of the atoms is the same but which differ in the arrangement of the atoms in space are termed "stereoisomers". Stereoisomers that are not mirror images of one another are termed "diastereomers". Stereoisomers that are non-superimposable mirror images of each other are termed "enantiomers". When a compound comprises an asymmetric center (i.e. chiral center), for example, a carbon atom bonded to four different groups, a pair of enantiomers is possible. An enantiomer can be characterized by the absolute configuration of its asymmetric center, which is designated by the Cahn-Ingold-Prelog R- and S-sequence rules. Alternatively, an enantiomer can be characterized by the manner in which it rotates the plane of polarized light, designated as dextrorotatory [(+)-enantiomer] or levorotatory [(−)-enantiomer]. A chiral compound can exist as either individual enantiomer or as a mixture thereof. A mixture containing equal proportions of enantiomers is called a "racemic mixture".

As generally understood by those of skill in the art, an optically pure compound is one that is enantiomerically pure. As used in this specification, the term "optically pure" refers to a compound comprising a substantial excess of a single enantiomer. In an embodiment, "optically pure" refers to a compound comprising at least 85% of a single isomer (70% e.e.). In an embodiment, "optically pure" refers to a compound comprising at least 90% of a single isomer (80% e.e.). In an embodiment, "optically pure" refers to a compound comprising at least 95% of a single isomer (90% e.e.). In an embodiment, "optically pure" refers to a compound comprising at least 97.5% of a single isomer (95% e.e.). In an embodiment, "optically pure" refers to a compound comprising at least 99% of a single isomer (98% e.e.).

The invention contemplates that for any stereocenter or axis of chirality for which stereochemistry has not been defined, that stereocenter or axis of chirality can be present in its R form, S form, or as a mixture of the R and S forms.

The present specification refers to a number of chemical terms and abbreviations used by those skilled in the art. Nevertheless, definitions of selected terms are provided for clarity and consistency.

Abbreviations: NMR: Nuclear Magnetic Resonance; MS: Mass Spectrometry; m.p.: melting point; HRMS: High Resolution Mass Spectrometry; FAB: Fast Atom Bombardment; Ac: Acetyl; AcOH: Acetic acid; $CH_2Cl_2$: Dichloromethane; $CDCl_3$: Chloroform-d; DCM: Dichloromethane; DMF: Dimethylformamide; DBU: 1,8-diazabicyclo[5.4.0]undec-7-ene; DDQ: 2,3-Dichloro-5,6-dicyano-p-benzoquinone; EtOAc: Ethyl acetate; Ph: Phenyl; THF: Tetrahydrofuran; Tf: Trifluoromethanesulfonyl; TFA: Trifluoroacetic acid; TBDPS: t-Butyldiphenylsilyl; and TLC: Thin Layer Chromatography.

In an embodiment, the ligands of the present invention are prepared using low-cost reagents that facilitate both synthesis and isolation. In a further embodiment, the ligands of general Formula I are prepared in optically pure form such that asymmetric reactions can be effectively achieved.

Dihydroisoquinoline derivatives widely exist in nature and exhibit a broad range of biological and pharmaceutical properties.[7] In an embodiment, the present invention relates to a novel class of chiral ligands based on the 1-(3,4-dihydroisoquinolin-1-yl)-naphthalene core structure. In a further embodiment, the present invention relates to a novel class of ligands of general Formula I:

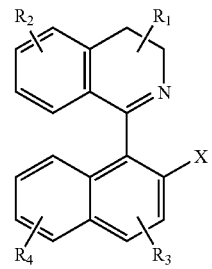

Formula I wherein:
$R_1$, $R_2$, $R_3$ and $R_4$, are independently selected from the group consisting of hydrogen, halogen, hydroxy, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkylthio, $C(O)R_5$, $C(O)OR_5$, $C(O)NHR_5$, $Si(R_5)_3$, benzyl and aryl;

X is selected from the group consisting of Cl, Br, I, $OR_6$, O-Prot, $OPR_6$, $P(R_6)_2$, $NHR_6$, $N(R_6)_2$, $NHCSNHR_6$, $NHCONHR_6$, and $SR_6$; and $R_5$ and $R_6$ are selected from the group consisting of hydrogen, $C_{1-10}$ alkyl, $C_{2-10}$ alkenyl, $C_{2-10}$ alkynyl, $C_{1-10}$ alkoxy, phenyl, and aryl.

Non-limiting examples of ligands of general Formula I are illustrated herein below in Scheme 2.

Scheme 2

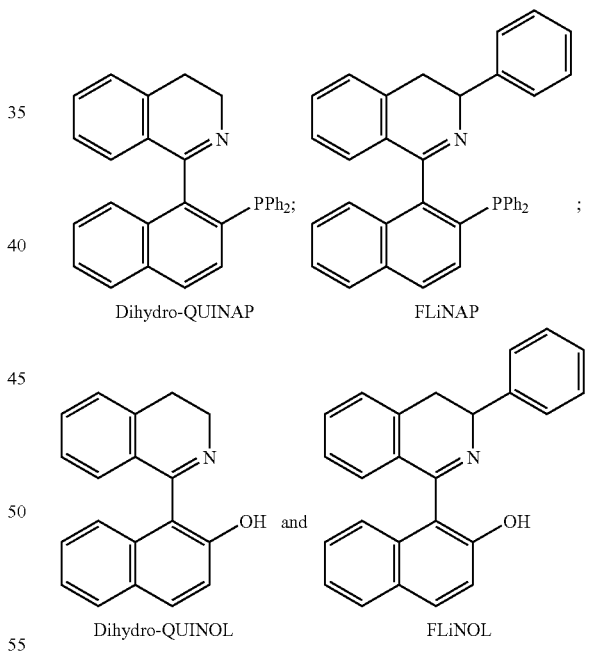

Dihydro-QUINAP    FLiNAP

Dihydro-QUINOL    FLiNOL

The ligands of the present invention can be further modified by yet other substituents. Such other substituents are known in the art, and are within the capacity of a skilled technician. Non-limiting examples of such further substituents (e.g. $R_1$, $R_2$, $R_3$ and $R_4$) comprise —$CO_2H$, —$CO_2M$ (M is selected from the group of metal ions, ammonium ions and phosphonium ions) and —$CO_2R$; —$SO_3H$, —$SO_3M$ (M is selected from the group of metal ions, ammonium ions and phosphonium ions) and —$SO_3R$; —$PO_3H_2$, —$PO_3M_2$ (M is selected from the group of metal ions, ammonium ions and phosphonium ions), and —$PO_3R_2$; —SH, —SM (M is selected from the group of metal ions, ammonium ions and phosphonium ions) and —SR; —OH, —OM (M is selected from the group of metal ions, ammonium ions and phosphonium ions) and —OR; —RCO$_2$H and —RCO$_2$M (M is selected from the group of metal ions, ammonium ions and phosphonium ions); —RSO$_3$H and —RSO$_3$M (M is selected from the group of metal ions, ammonium ions and phosphonium ions); —NH$_2$, —NHR, —N(R)$_2$, —NHCOR, —NHC(=)O—NHR and —NHC(=)S—NHR; —CN; —NO$_2$; —R—OH and R-OM (M is selected from the group of metal ions, ammonium ions and phosphonium ions); -aryl-SO$_3$H, -aryl-SO$_3$M (M is selected from the group of metal ions, ammonium ions and phosphonium ions) and -aryl-SO$_3$R; wherein R is a C$_{1-10}$ alkyl group.

In an embodiment, the present invention relates to a process for the preparation of a ligand of general Formula I:

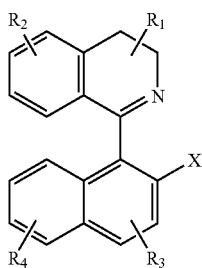

Formula I wherein:

R$_1$, R$_2$, R$_3$ and R$_4$, are independently selected from the group consisting of hydrogen, halogen, hydroxy, C$_1$-C$_{10}$ alkyl, C$_2$-C$_{10}$ alkenyl, C$_2$-C$_{10}$ alkynyl, C$_1$-C$_{10}$ alkoxy, C$_1$-C$_{10}$ alkylthio, C(O)R$_5$, C(O)OR$_5$, C(O)NHR$_5$, Si(R$_5$)$_3$, benzyl and aryl;

X is selected from the group consisting of Cl, Br, I, OR$_6$, O-Prot, OPR$_6$, P(R$_6$)$_2$, NHR$_6$, N(R$_6$)$_2$, NHCSNHR$_6$, NHCONHR$_6$, and SR$_6$; and R$_5$ and R$_6$ are selected from the group consisting of hydrogen, C$_{1-10}$ alkyl, C$_{2-10}$ alkenyl, C$_{2-10}$ alkynyl, C$_{1-10}$ alkoxy, phenyl, and aryl;

comprising:

i) reacting a tetrahydroisoquinoline derivative of general Formula Ia:

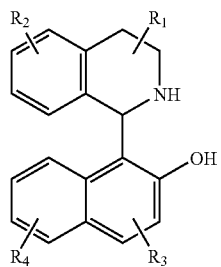

Formula Ia wherein:

R$_1$, R$_2$, R$_3$ and R$_4$, are independently selected from the group consisting of hydrogen, halogen, hydroxy, C$_1$-C$_{10}$ alkyl, C$_2$-C$_{10}$ alkenyl, C$_2$-C$_{10}$ alkynyl, C$_1$-C$_{10}$ alkoxy, C$_1$-C$_{10}$ alkylthio, C(O)R$_5$, C(O)OR$_5$, C(O)NHR$_5$, Si(R$_5$)$_3$, benzyl and aryl; and R$_5$ is selected from the group consisting of hydrogen, C$_{1-10}$ alkyl, C$_{2-10}$ alkenyl, C$_{2-10}$ alkynyl, C$_{1-10}$ alkoxy, phenyl, and aryl;

with a triflating reagent to produce a compound of general Formula Ib

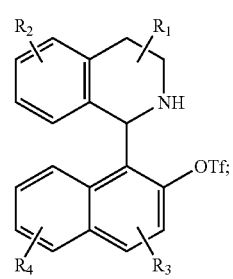

Formula Ib ii) reacting the compound of general Formula Ib with an oxidizing agent to produce a dihydroisoquinoline derivative of general formula Ic;

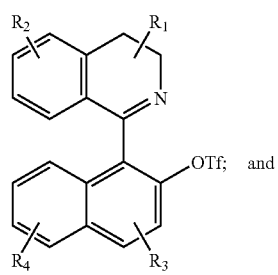

Formula Ic and iii) converting the dihydroisoquinoline of general formula Ic to produce a dihydroisoquinoline ligand of general Formula I (Scheme 3).

Scheme 3

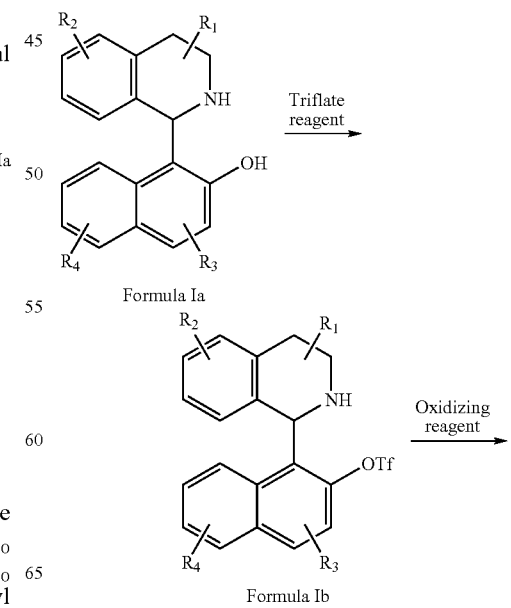

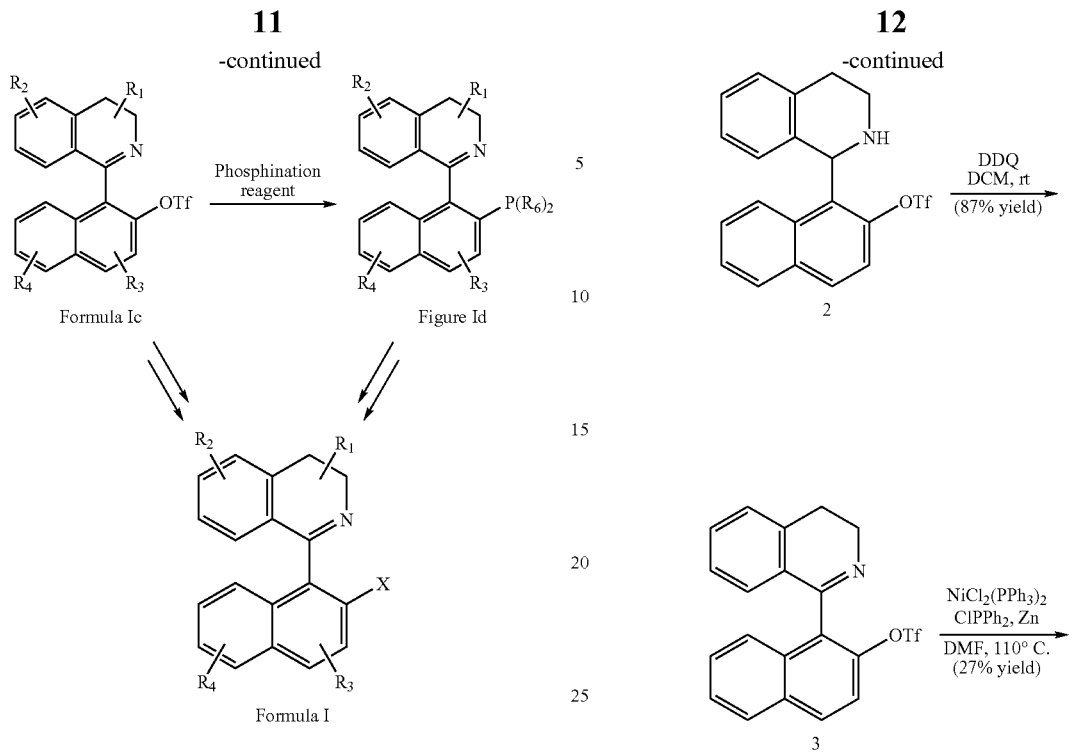

In an embodiment of the present invention, the dihydroisoquinoline of general formula Ic is further reacted with a phosphinating reagent to produce a dihydroisoquinoline of general formula Id which is subsequently converted into a dihydroisoquinoline derivative of general Formula I (Scheme 3).

In an embodiment of the present invention, the process further comprises isolating an optically pure form of a ligand of general Formula I.

In an embodiment of the present invention, the chiral ligands are used in conjunction with a chiral auxiliary. In a further embodiment of the present invention, the chiral ligands are used in conjunction with a solid support (e.g. silica gel, polymer). In a further embodiment of the present invention, the chiral ligands are used in conjunction with ionic liquids (liquid support). In a further embodiment of the present invention, the chiral ligands are used in conjunction with perfluoroalkyls (solution-phase synthesis based on fluorinated (fluorous) soluble supports).

The present invention relates to chiral ligands based on the 1-(3,4-dihydroisoquinolin-1-yl)-naphthalene core structure. In an embodiment, the present invention relates to dihydro-QUINAP as well as to a process for its preparation (Scheme 4).

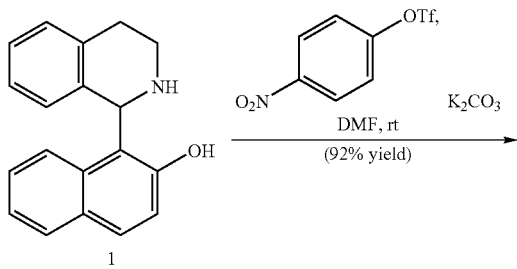

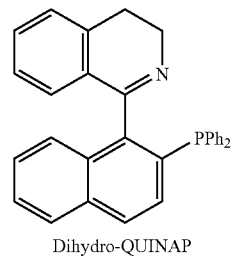

Tetrahydroisoquinoline 1 was selectively triflated to provide triflate 2 in 92% yield. A non-limiting example of a suitable triflating reagent comprises 4-nitrophenyl trifluoromethanesulfonate.[8] Other suitable triflating agents are known in the art, and are within the capacity of a skilled technician. Triflate 2 was then treated with an oxidizing agent to provide imine 3 in 87% yield. A non-limiting example of a suitable oxidizing agent comprises DDQ. Other suitable oxidizing agents are known in the art, and are within the capacity of a skilled technician. Imine 3 was then treated with a phosphinating agent to provide dihydro-QUINAP in 27% yield. A non-limiting example of a suitable phosphinating agent comprises the reagent mixture Ni(PPh$_3$)$_2$Cl$_2$, Zn and PPh$_2$Cl. Other suitable phosphinating agents are known in the art, and are within the capacity of a skilled technician.

The present invention relates to chiral ligands based on the 1-(3,4-dihydroisoquinolin-1-yl)-naphthalene core structure. In an embodiment, the present invention relates to a phenyl substituted dihydro-QUINAP (i.e. FLiNAP) as well as to a process for its preparation (Scheme 5). In yet a further embodiment, the present invention relates to a phenyl substituted dihydro-QUINOL (i.e. FLiNOL) as well as to a process for its preparation (Scheme 5).

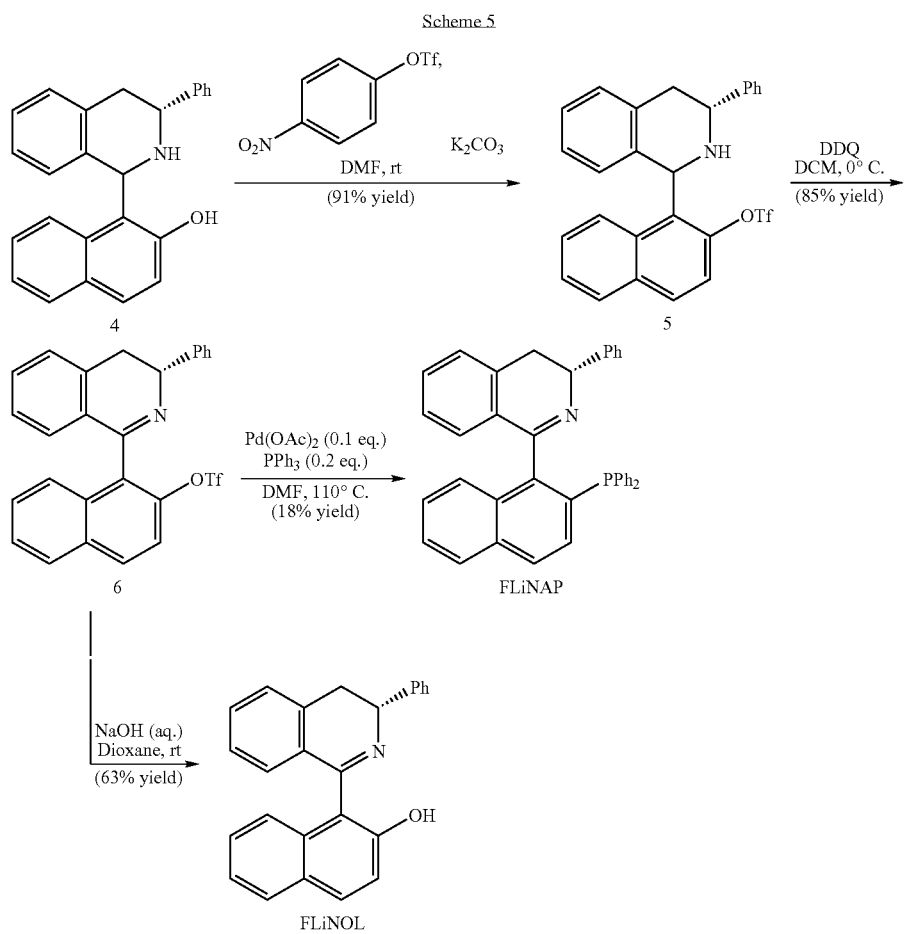

Scheme 5

Tetrahydroisoquinoline 4 was selectively triflated to provide triflate 5 in 92% yield. A non-limiting example of a suitable triflating reagent comprises 4-nitrophenyl trifluoromethanesulfonate.[8] Other suitable triflating agents are known in the art, and are within the capacity of a skilled technician. Triflate 5 was then treated with an oxidizing agent to provide imine 6 in 85% yield. A non-limiting example of a suitable oxidizing agent comprises DDQ. Other suitable oxidizing agents are known in the art, and are within the capacity of a skilled technician. Imine 6 was then treated with a phosphinating agent to provide FLiNAP in 18% yield. A non-limiting example of a suitable phosphinating agent comprises the reagent mixture Pd(OAc)$_2$ and PPh$_3$. Other suitable phosphinating agents are known in the art, and are within the capacity of a skilled technician. Alternatively, imine 6 was treated with a hydrolyzing agent to provide FLiNOL in 63% yield. A non-limiting example of a suitable hydrolyzing agent comprises NaOH. Other suitable hydrolyzing agents are known in the art, and are within the capacity of a skilled technician.

In an embodiment of the present disclosure, the chiral ligands are used in catalytic asymmetric reactions. In a further embodiment of the present invention, the chiral ligands are used in catalytic asymmetric reactions to provide optically pure products. In yet a further embodiment of the present invention, the chiral ligands are used in the asymmetric synthesis of biological compounds. In a particular embodiment of the present invention, the biological compounds have therapeutic and/or prophylactic properties. In a further particular embodiment of the present invention, the chiral ligands are used in catalytic asymmetric three-component coupling reactions of aldehydes, amines and alkynes (i.e. A$^3$ reactions) (Scheme 6).[9]

Scheme 6

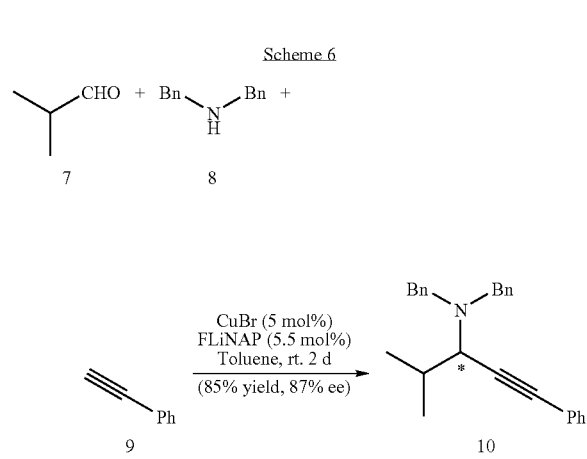

FLiNAP was used in the catalytic asymmetric three-component coupling reaction of 2-methylpropanal (7), N,N-dibenzylamine (8) and phenylacetylene (9), to provide coupling product 10 in 85% yield and 87% ee.

EXPERIMENTAL

General information: $^1$H NMR spectra were recorded on Varian 300 and 400 MHz spectrometers and the chemical shifts were reported in parts per million (δ) relative to internal standard TMS (0 ppm) for CDCl$_3$. The peak patterns are indicated as follows: s, singlet; brs, broad singlet; d, doublet; t, triplet; dt, doublet of triplet; dq, doublet of quartet; ddd, doublet of doublet of doublet; dtd, doublet of triplet of doublet; m, multiplet; q, quartet. The coupling constants, J, are reported in Hertz (Hz). $^{13}$C NMR spectra were recorded using 75 and 100 MHz spectrometers and the chemical shifts were reported in parts per million (δ) relative to internal standard solvent signals for CDCl$_3$ (central peak is 77.00 ppm in CDCl$_3$). HRMS were obtained using a Kratos MS25RFA Mass Spectrometer. IR spectra were recorded using an ABB Bomem MB100 instrument. Melting points were recorded using a Melting Point Apparatus, Gallenkamp. All reagents were weighed and handled in air at room temperature. All regents were purchased from Aldrich except 3,4-dihydroisoquinoline and (R)-3,4-dihydro-phenylisoquinoline which were prepared according to literature methods.[10] All reagents were used without further purification. The enantiomeric excess (ee) was determined using a Chiralcel OD-H HPLC column (1/99 isopropanol/hexane).

Procedure for the Preparation of 1-(1,2,3,4-Tetrahydroisoquinolin-1-yl)-naphthalene-2-yl trifluoromethanesulfonate (2)

Powdered K$_2$CO$_3$ (2.30 g, 17 mmol) was added to a solution of 1 (2.30 g, 8.4 mmol) and 4-nitrophenyl trifluoromethanesulfonate (2.28 g, 8.4 mmol) in DMF (70 mL). After 3 hours, the mixture was poured into water (300 mL) and extracted with CH$_2$Cl$_2$ (250 mL, 3 times). The combined organic fractions were dried over sodium sulfate, filtered, and concentrated to provide crude 2 as an oil which was purified by column chromatography on silica gel (5:1 hexanes/EtOAc). The fractions containing the product (R$_f$=0.50, 5:1 hexanes/EtOAc) were collected and concentrated under reduced pressure to yield the title product 2 (3.15 g, 92% yield) as an oil. $^1$H NMR (CDCl$_3$, 400 MHz, ppm): δ 8.18 (d, J=8.8 Hz, 1H), 7.92-7.83 (m, 2H), 7.46-7.11 (m, 5H), 6.92 (t, J=7.2 Hz, 1H), 6.51 (d, J=7.6 Hz, 1H), 5.97 (s, 1H), 3.54-3.28 (m, 3H), 2.94 (d, J=14.8, 1H), 2.31 (s, 1H); $^{13}$C NMR (CDCl$_3$, 75 MHz, ppm): δ 146.03, 137.81, 134.57, 133.68, 131.97, 131.48, 131.02, 129.22, 128.45, 128.07, 126.71, 126.59, 126.32, 126.11, 120.75, 118.98, 116.51, 55.86, 44.96, 29.67.

Procedure for the Preparation of 1-(3,4-Dihydroisoquinolin-1-yl)-naphthalene-2-yl trifluoromethanesulfonate (3)

Powdered 2,3-dichloro-5,6-dicyano-p-benzoquinone (DDQ) (46 mg, 0.2 mmol) was added to a solution of 2 (82 mg, 0.2 mmol) in CH$_2$Cl$_2$ (2 mL) at rt. After 20 minutes, the mixture was filtered through a short pad of silica gel using CH$_2$Cl$_2$ as the eluant. The solvent was evaporated and the residue was purified by column chromatography on silica gel (5:1 hexanes/EtOAc). The fractions containing the product (R$_f$=0.4) were collected and concentrated to yield the title product 3 (70 mg, 87% yield) as an oil. $^1$H NMR (CDCl$_3$, 400 MHz, ppm): δ 8.02 (d, J=8.8 Hz, 1H), 7.95 (d, J=8.4, 1H), 7.71 (d, J=8.0, 1H), 7.58-7.26 (m, 5H), 7.11 (t, J=7.2 Hz, 1H), 6.76 (d, J=8.0 Hz, 1H), 4.17-4.09 (m, 2H), 3.05-2.98 (m, 2H); $^{13}$C NMR (CDCl$_3$, 100 MHz, ppm): δ 162.51, 144.46, 137.08, 132.42, 131.43, 130.95, 129.52, 129.14, 128.21, 127.83, 127.61, 121.14, 127.09, 126.88, 126.09, 119.95, 119.28, 116.77, 47.93, 25.57.

Procedure for the Preparation of dihydro-QUINAP

To a solution of 3 (40 mg, 0.1 mmol) and bis(triphenylphosphine) nickel(II) chloride (33 mg, 0.05 mmol) in dry DMF (1 mL) under nitrogen was added chlorodiphenylphosphine (18 µL, 0.1 mmol). Zn dust (14 mg, 0.2 mmol) was subsequently added. The solution was heated to 110° C. under nitrogen for 12 h. The reaction mixture was then cooled and the solvent was removed by vacuum evaporation. The residue was redissolved in dichloromethane and purified by means of a TLC plate (4:1 hexanes/EtOAc). The fractions containing the product (R$_f$=0.5) were collected and concentrated to yield the title product (12 mg, 27% yield) as a solid. $^1$H NMR (400 MHz, CDCl$_3$): δ 7.84-7.79 (m, 2H), 7.73 (d, J=8.0 Hz, 1H), 7.62-7.16 (m, 15H), 6.94 (m, 1H), 6.69 (d, J=7.2 Hz, 1H), 4.05-3.80 (m, 2H), 3.04-2.88 (m, 2H); $^{31}$P NMR (121.46 MHz, CDCl$_3$): δ −12.7.

Procedure for the Preparation of dihydro-QUINOL

A round-bottomed flask (100 mL) containing a magnetic stirrer was charged with 3 (81 mg, 0.2 mmol), 1,4-dioxane (3 mL) and methanol (1.4 mL). An aqueous sodium hydroxide solution (1.4 mL, 3N) was subsequently added. The reaction mixture was stirred for 6 hours and acidified (to pH 7) by the addition of a few drops of a diluted hydrochloric acid solution. The reaction mixture was twice extracted with EtOAc and the combined organic fractions dried over magnesium sulfate and concentrated to afford the title compound as a yellow solid (41 mg; 76%). HRMS calcd. for C$_{19}$H$_{16}$NO$^{+1}$ (M+1): 274.1232. found: 274.1226.

Procedure for the Preparation of 1-((3R)-1,2,3,4-Tetrahydro-3-phenylisoquinolin-1-yl)-naphthalen-2-yl trifluoromethanesulfonate (5)

2-Naphthol (2.09 g, 14.5 mmol) was placed in a flask under nitrogen and (R)-3,4-dihydro-3-phenylisoquinoline 3.0 g (14.5 mmol) was added. The resulting mixture was stirred overnight at 80° C., whereupon no liquid remained. The resulting mixture was recrystallized from Et$_2$O and collected to yield product 4 (4.12 g, 81% yield) as a solid. $^1$H NMR (CDCl$_3$, 400 MHz, ppm): δ 11.85 (s, 1H), 8.09 (d, J=8.8 Hz, 1H), 7.84 (dd, J=8.4 Hz, J=31.2 Hz, 2H), 7.56-7.12 (m, 10H), 6.97-6.93 (m, 1H), 6.72 (d, J=8.0 Hz, 1H), 6.03 (s, 1H), 4.36 (dd, J=3.6 Hz, J=11.2 Hz, 1H), 3.38 (m, 1H), 3.16 (d, J=14.4 Hz, 1H), 2.80 (s, 1H); $^{13}$C NMR (CDCl$_3$, 100 MHz, ppm): δ 155.74, 142.57, 135.61, 133.98, 133.37, 129.88, 128.89, 128.57, 128.37, 128.09, 127.01, 126.88, 126.84, 126.48, 122.67, 121.39, 120.12, 118.11, 59.31, 56.68, 38.38; HRMS calcd. for C$_{25}$H$_{22}$NO$^{+1}$ (M+1): 352.1701. found: 275.1696.

Powdered K$_2$CO$_3$ (787 mg, 5.7 mmol) was added to a solution of 4 (1.0 g, 2.85 mmol) and 4-nitrophenyl trifluoromethanesulfonate (772 mg, 2.85 mmol) in DMF (20 mL). The reaction mixture was stirred overnight at room temperature. Water (30 mL) was subsequently added and the mixture extracted with ethyl acetate (30 mL, 3 times). The combined organic fractions were dried over sodium sulfate, filtered and concentrated to provide crude 5 which was subsequently purified by column chromatography on silica gel (1:9 EtOAc/hexanes) to yield the title product 5 (1.30 g, 94% yield) as a solid. $^1$H NMR (CDCl$_3$, 400 MHz, ppm): δ 8.41 (d, J=8.4 Hz, 1H), 7.92 (d, J=8.8 Hz, 1H), 7.85 (d, J=7.6 Hz, 1H), 7.52-7.13

(m, 10H), 6.94 (t, J=7.2 Hz, 1H), 6.56 (d, J=7.6 Hz, 1H), 6.20 (s, 1H), 4.39 (dd, J=3.6, J=11.6, 1H), 3.42 (m, 1H), 3.18 (dd, J=3.6 Hz, J=16.4, 1H), 2.40 (s, 1H); $^{13}$C NMR (CDCl$_3$, 100 MHz, ppm): δ 146.00, 144.10, 137.26, 134.59, 133.77, 132.06, 131.31, 131.10, 128.98, 128.83, 128.57, 128.29, 127.54, 126.93, 126.64, 126.60, 126.43, 126.32, 126.13, 120.24, 118.86, 59.73, 56.80, 38.71; HRMS calcd for $C_{26}H_{21}F_3NO_3S^{+1}$ (M+1): 484.1194. found: 484.1189.

Procedure for the Preparation of 1-((R)-3,4-Dihydro-3-phenylisoquinolin-1-yl)-naphthalen-2-yl trifluoromethanesulfonate (6)

Powdered 2,3-dichloro-5,6-dicyano-p-benzoquinone (DDQ) (908 mg, 4.0 mmol) was added to a solution of 5 (2.033 g, 4.21 mmol) in CH$_2$Cl$_2$ (20 mL) at rt. After 20 minutes, the mixture was filtered through a short pad of silica gel using CH$_2$Cl$_2$ as the eluant. The solvent was evaporated and the residue was purified by column chromatography on silica gel (9:1 hexanes/EtOAc) to yield the title product 6 (1.65 g, 86% yield) as a solid. $^1$H NMR (CDCl$_3$, 400 MHz, ppm): δ 8.03-7.93 (m, 2H), 7.54-7.12 (m, 12H), 6.86-6.79 (m, 1H), 5.04-4.94 (m, 1H), 3.29-3.06 (m, 2H); HRMS calcd for $C_{26}H_{19}F_3NO_3S^{+1}$ (M+1): 482.1038. found: 482.1032.

Procedure for the Preparation of FLiNAP 1-((R)-3,4-Dihydro-3-phenylisoquinolin-1-yl)-naphthalen-2-yl trifluoromethanesulfonate 6 (370 mg, 0.77 mmol), palladium(II) acetate (17.3 mg, 0.077 mmol) and triphenylphosphine (464 mg, 1.77 mmol) were dissolved in DMF (3 mL) in a Teflon screw-capped flask placed under nitrogen. The reaction mixture was heated to 110-115° C. for 3 days. The color of the solution changed from pale yellow to red. The residue was purified by column chromatography on silica gel (20:1 hexanes/EtOAc) to yield the title compound FLiNAP (71 mg, 18% yield) as a solid. $^1$H NMR (CDCl$_3$, 400 MHz, ppm): δ 7.96-6.85 (m, 25H), 4.97-4.88 (m, 1H), 3.31-2.99 (m, 2H); HRMS calcd. for $C_{37}H_{29}NP^{+1}$ (M+1): 518.2038. found: 518.2032. $^{31}$P NMR (121.46 MHz, CDCl$_3$): δ −13.3.

Procedure for the Preparation of FLiNOL

A round-bottomed flask (100 mL) containing a magnetic stirrer was charged with 6 (96 mg, 0.2 mmol), 1,4-dioxane (3 mL) and methanol (1.4 mL). An aqueous sodium hydroxide solution (1.4 mL, 3N) was subsequently added. The reaction mixture was stirred for 6 hours and acidified (to pH 7) by the addition of a few drops of a diluted hydrochloric acid solution. The reaction mixture was twice extracted with EtOAc and the combined organic fractions dried over magnesium sulfate and concentrated to afford the title compound as a yellow solid (44 mg; 63%). HRMS calcd. for $C_{25}H_{20}NO^{+1}$ (M+1): 350.1545. found: 350.1539.

Procedure for the preparation of N,N-Dibenzyl-4-methyl-1-phenyl-1-pentyn-3-amine (10)

In a dry, argon flushed 5 mL flask, equipped with a magnetic stirrer and a septum, CuBr (1.5 mg, 0.01 mmol, 5 mol %) and (R)(+)-FLiNAP (5.7 mg, 0.011 mmol, 5.5 mol %) were suspended in dry toluene (1 mL) and stirred for 30 min. Phenylacetylene (9) (21 mg, 0.2 mmol), 2-methylpropanal (7) (15 mg, 0.2 mmol) and dibenzylamine (8) (40 mg, 0.2 mmol) were then added. The reaction mixture was stirred at room temperature for 2 days. The crude product was concentrated under reduced pressure and purified by column chromatography on silica gel (95:5 pentane/ether) to yield the title compound 10 as an enantiomeric mixture. The enantiomers were subsequently separated using HPLC [(Chiralcel OD-H, 99% n-heptane/1% i-propanol, 0.2 mL/min): t, (min)=19.94 (−), 20.98 (+)]. The (−) isomer was isolated as an oil (60 mg, 85% yield, 87% ee).

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

REFERENCES

1. For an overview see Noyori, R, *Adv. Synth. Catal.* 2003, 345, 15.
2. Takaya H, Akutagawa S, Noyori, R, *Org. Synth., Coll. Vol. VIII* 1993, 57.
3. (a) Valk J M, Whitlock G A, Layzell, T. P.; Brown J M, *Tetrahedron. Asymmetry* 1995, 6, 2593; (b) Fernandez E, Maeda K, Hooper M W, Brown J M, *Chem.-Eur. J.* 2000, 6, 1840.
4. Brunel J M, *Chem. Rev.* 2005, 105, 4233.
5. Macleod P D, Li Z, Feng J, Li C-J, *Tetrahedron Lett.* 2006, 47, 6791.
6. Feng J, Bohle, D S, Li C-J, *Tetrahedron: Asymmetry* 2007, 18, 1043.
7. (a) Alvarez M, Joule J A, *Science of Synthesis* 2005, 15, 661; (b) Chrzanowska M, Rozwadowska M D, *Chem. Rev.* 2004, 104, 3341.
8. (a) Stille J K, Echavarren A M, Williams Robert M, Hendrix J A, *Organic Syntheses* 1993, 71, 97; (b) Zhu J, Bigot A, Dau METH, *Tetrahedron Lett.* 1997, 38, 1181.
9. Gommermann N, Koradin C, Polborn K, Knochel P, *Angew. Chem. Int. Ed.* 2003, 42, 5763.
10. a) Pelletier J C, Cava M P. *J. Org. Chem.* 1987, 52, 616; (b) Larsen R D, Reamer, R A, Corley E G, Davis P, Grabowski E J J, Reider P J, Shinkai I. *J. Org. Chem.* 1991, 56, 6034.

What is claimed is:
1. A ligand of Formula I:

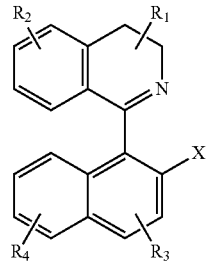

Formula I wherein:
a) $R_1$, $R_2$, $R_3$ and $R_4$, are independently selected from the group consisting of hydrogen, halogen, hydroxy, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkylthio, $C(O)R_5$, $C(O)OR_5$, $C(O)NHR_5$, $Si(R_5)_3$, benzyl and aryl;

b) X is selected from the group consisting of Cl, Br, I, OR$_6$, O-Prot, OPR$_6$, P(R$_6$)$_2$, NHR$_6$, N(R$_6$)$_2$, NHCSNHR$_6$, NHCONHR$_6$ and SR$_6$; and
c) R$_5$ and R$_6$ are independently selected from the group consisting of hydrogen, C$_{1-10}$ alkyl, C$_{2-10}$ alkenyl, C$_{2-10}$ alkynyl, C$_{1-10}$ alkoxy, phenyl, and aryl.
2. The ligand of claim 1, wherein said ligand is selected from the group consisting of:
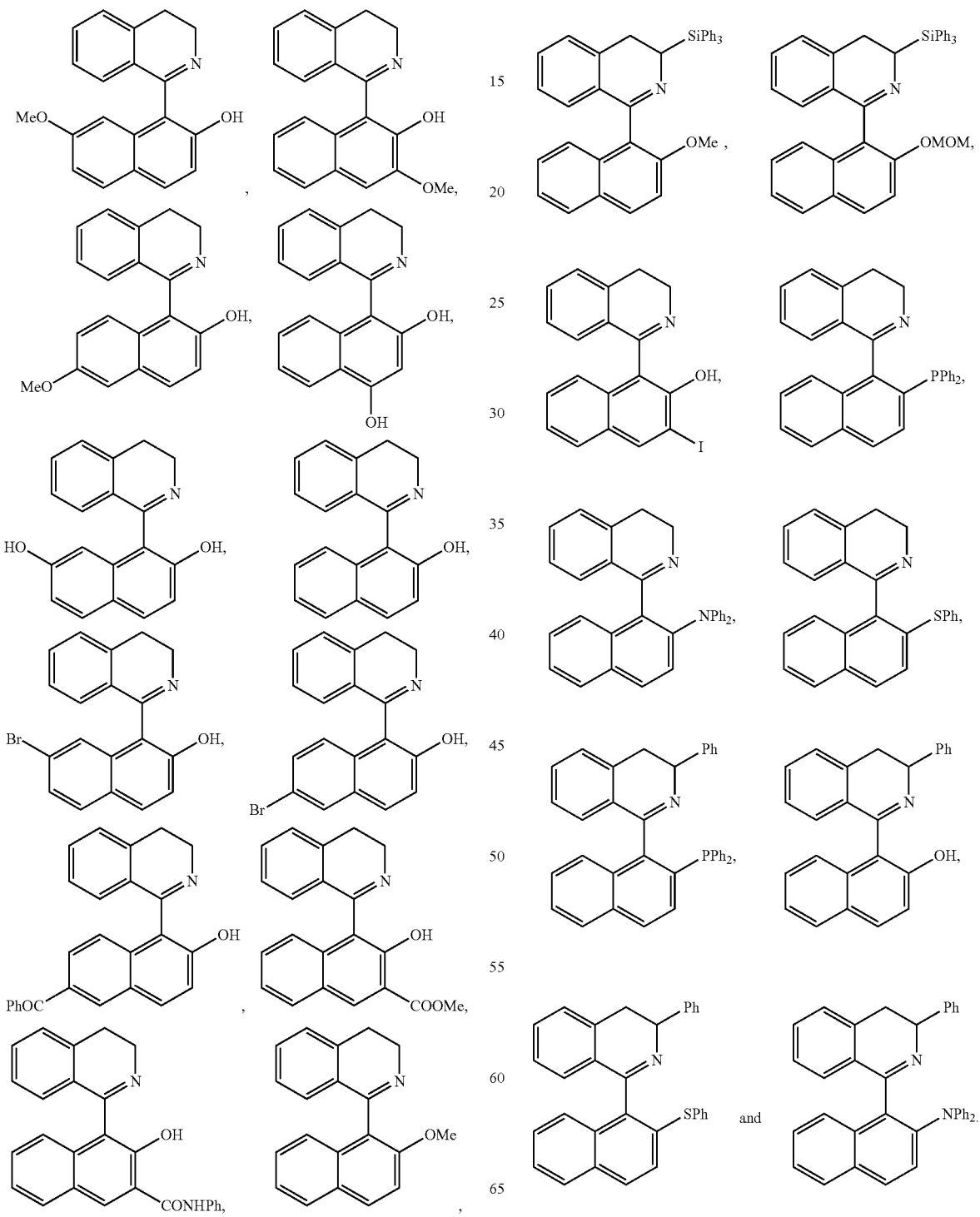

3. The ligand of claim 2, wherein said ligand is selected from the group consisting of:

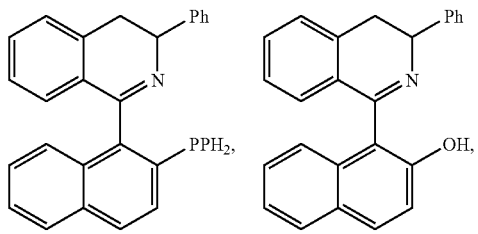

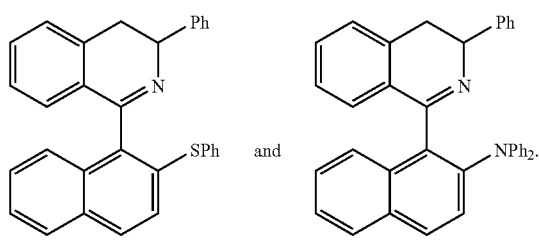

4. The ligand of claim 3, wherein said ligand is a racemic mixture of enantiomers.

5. The ligand of claim 3, wherein said ligand is a non-racemic mixture of enantiomers.

6. The ligand of claim 3, wherein said ligand comprises the L-enantiomer.

7. The ligand of claim 3, wherein said ligand comprises the R-enantiomer.

8. The ligand of claim 6, wherein the optical purity of said ligand is at least 50% ee.

9. The ligand of claim 6, wherein the optical purity of said ligand is at least 60% ee.

10. The ligand of claim 6, wherein the optical purity of said ligand is at least 70% ee.

11. The ligand of claim 6, wherein the optical purity of said ligand is at least 80% ee.

12. The ligand of claim 6, wherein the optical purity of said ligand is at least 90% ee.

13. The ligand of claim 6, wherein the optical purity of said ligand is at least 95% ee.

14. The ligand of claim 7, wherein the optical purity of said ligand is at least 50% ee.

15. The ligand of claim 7, wherein the optical purity of said ligand is at least 60% ee.

16. The ligand of claim 7, wherein the optical purity of said ligand is at least 70% ee.

17. The ligand of claim 7, wherein the optical purity of said ligand is at least 80% ee.

18. The ligand of claim 7, wherein the optical purity of said ligand is at least 90% ee.

19. The ligand of claim 7, wherein the optical purity of said ligand is at least 95% ee.

20. A process for the preparation of a ligand of Formula I as defined in claim 1, the process comprising:
a) reacting a compound of general Formula Ia:

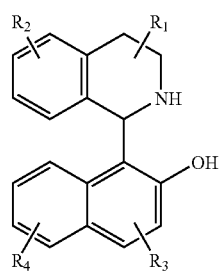

Formula Ia wherein:
i) $R_1$, $R_2$, $R_3$ and $R_4$, are independently selected from the group consisting of hydrogen, halogen, hydroxy, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkylthio, $C(O)R_5$, $C(O)OR_5$, $C(O)NHR_5$, $Si(R_5)_3$, benzyl and aryl; and
ii) $R_5$ is selected from the group consisting of hydrogen, $C_{1-10}$ alkyl, $C_{2-10}$ alkenyl, $C_{2-10}$ alkynyl, $C_{1-10}$ alkoxy, phenyl, and aryl;

with a triflating reagent to produce a compound of general Formula Ib:

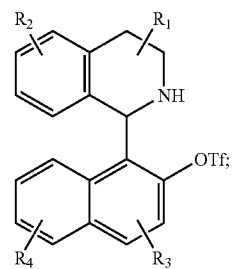

Formula Ib ii) reacting the compound of general Formula Ib with an oxidant to produce a compound of general Formula Ic:

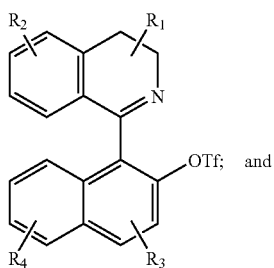

Formula Ic iii) converting the triflate to produce a ligand of general Formula I.

21. The process of claim 20, further comprises isolating an optically pure form of a ligand of Formula I.

* * * * *

UNITED STATES PATENT AND TRADEMARK OFFICE
CERTIFICATE OF CORRECTION

PATENT NO. : 8,183,378 B2  
APPLICATION NO. : 12/267285  
DATED : May 22, 2012  
INVENTOR(S) : Chao-Jun Li et al.

Page 1 of 1

It is certified that error appears in the above-identified patent and that said Letters Patent is hereby corrected as shown below:

In claim 3, column 21, lines 3-28, delete chemical drawings and insert

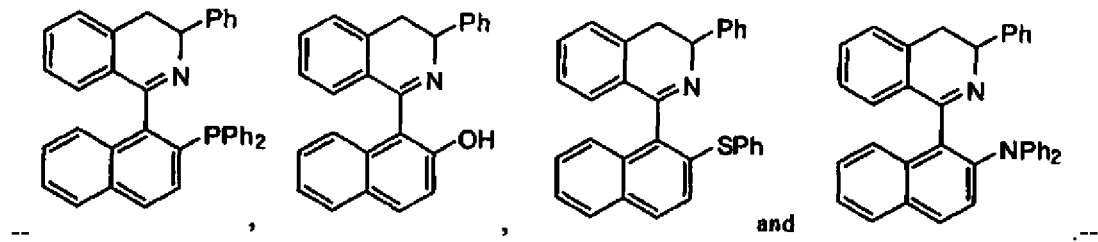

therefor.

Signed and Sealed this  
Twenty-eighth Day of August, 2012

David J. Kappos  
*Director of the United States Patent and Trademark Office*